(12) United States Patent  (10) Patent No.: US 7,670,003 B2
Kendrick                      (45) Date of Patent:      Mar. 2, 2010

(54) EXAMINATION ASSEMBLY WITH IMPROVED ACCESS FOR THE WHEELCHAIR BOUND PATIENT

(75) Inventor: Ronald M. Kendrick, Toledo, OH (US)

(73) Assignee: Ophthalmology Associates of Northwestern Ohio, Inc., Maumee, OH (US)

( * ) Notice: Subject to any disclaimer, the term of this patent is extended or adjusted under 35 U.S.C. 154(b) by 298 days.

(21) Appl. No.: 11/828,387

(22) Filed: Jul. 26, 2007

(65) Prior Publication Data

US 2009/0027619 A1  Jan. 29, 2009

(51) Int. Cl.
*A61B 3/10* (2006.01)
*A61B 3/00* (2006.01)

(52) U.S. Cl. .................... 351/214; 351/200; 351/245

(58) Field of Classification Search .......... 351/200, 351/214, 244–245
See application file for complete search history.

(56) References Cited

U.S. PATENT DOCUMENTS

| | | | |
|---|---|---|---|
| 2,999,422 A | 9/1961 | Papritz | |
| 3,403,957 A | 10/1968 | Wilkinson | |
| 3,407,019 A | 10/1968 | Wilkinson | |
| 3,463,579 A | 8/1969 | Papritz | |
| 3,749,481 A | 7/1973 | Bosack et al. | |
| 3,871,753 A | 3/1975 | Papritz et al. | |
| 3,944,343 A | 3/1976 | Mueller, Jr. | |
| 4,331,392 A | 5/1982 | Sato | |
| 4,464,801 A | 8/1984 | Lamb | |
| D295,556 S | 5/1988 | Speaker | |
| 4,796,859 A | 1/1989 | Ventura | |
| 5,016,854 A | 5/1991 | Papritz et al. | |
| 5,196,874 A | 3/1993 | Muller et al. | |
| 5,216,456 A | 6/1993 | Volk | |
| 5,609,316 A * | 3/1997 | Tigliev | .................. 248/123.11 |
| D378,635 S | 4/1997 | Studer et al. | |
| D410,661 S | 6/1999 | Wolf | |
| 6,072,623 A | 6/2000 | Kitajima et al. | |
| 6,474,815 B1 | 11/2002 | Ulbers | |
| 6,644,810 B1 | 11/2003 | Ulbers | |
| 6,872,202 B2 | 3/2005 | Gerlach et al. | |
| 7,083,281 B2 | 8/2006 | Yogesan et al. | |
| 7,118,217 B2 | 10/2006 | Barker | |
| 7,174,982 B2 | 2/2007 | Kraus | |
| 2003/0004418 A1 | 1/2003 | Marmorstein | |
| 2005/0182327 A1 | 8/2005 | Petty et al. | |
| 2007/0132952 A1 | 6/2007 | Davis | |

\* cited by examiner

*Primary Examiner*—Scott J Sugarman
*Assistant Examiner*—Dawayne A Pinkney
(74) *Attorney, Agent, or Firm*—Robert K. Ruth, Esq.

(57) ABSTRACT

An examination assembly advantageous for use with wheelchair bound patients comprises a rotatable stand which receives medical equipment, an arm assembly mounted on the stand comprising a main arm connected to the stand and an auxiliary arm operatively connected to the main arm, a table which mounts at least part of the medical equipment having a table area and an underside, and an S-bracket connecting the auxiliary arm to the table such that the auxiliary arm is remote from the table. The auxiliary arm is above the table and the S-bracket comprises a mounting flange, an underside flange and a linking flange connecting the mounting flange to the underside flange. Fasteners connect the underside flange to the table.

10 Claims, 4 Drawing Sheets

EXAMINATION ASSEMBLY WITH IMPROVED ACCESS FOR THE WHEELCHAIR BOUND PATIENT

FIELD OF THE INVENTION

This invention relates to a stand for medical equipment and more particularly to a stand which improves access to the medical equipment for wheelchair bound patients.

BACKGROUND OF THE INVENTION

Medical equipment for examination of a patient sometimes comprises an examination chair, a stand which supports some of the medical equipment, and a table which supports additional medical equipment. The table is connected to the stand via a series of adjustable arms. An example would be a slit lamp biomicroscope. The slit lamp is an instrument consisting of a high-intensity light source that can be focused to shine as a slit. It is used in conjunction with a microscope. The lamp helps examination by allowing a doctor to look at the anterior segment, or frontal structures of the human eye, which includes the eyelid, sclera, conjunctiva, iris, natural crystalline lens, and cornea. The binocular slit-lamp examination provides stereoscopic magnified view of the eye structures in striking detail, enabling exact anatomical diagnoses to be made for many eye conditions. Combined with special lenses the examination of retinal structures can be accomplished in detail. While a patient is seated in the examination chair, he rests his chin and forehead on a support (chin strap) to steady the head. Using the biomicroscope, the optometrist or opthalmologist then proceeds to examine the patient's eye. The slit lamp is mounted on the table, which is in turn adjustably connected to the stand. This adjustablity allows the doctor to treat patients of varying heights and sizes.

However, known medical equipment stands have several limitations in the range of patients which can be conveniently examined, especially with respect to patients confined to a wheelchair. For example, the table is typically too wide to be placed between the arms of a standard wheelchair. Also, the arms are designed to work with an examination chair which is much higher than standard wheelchairs, and therefore cannot get low enough to examine a patient bound to a wheelchair. Moreover, the arms are attached to the table on the underside of the table near the center of the table, such that the arm partially obstructs area below the table, requiring the table to be raised to clear over a patient's legs, for example. Typically a wheelchair bound patient needs to be lifted out of his wheelchair and moved to a separate examination chair. All of this makes known medical equipment stands inconvenient for wheelchair bound patients. It would be desirable to provide a patient examination assembly which is convenient for essentially all patients, including wheelchair bound patients.

SUMMARY OF THE INVENTION

In accordance with a first aspect, a patient examination assembly comprises a rotatable stand which receives medical equipment, an arm assembly mounted on the stand comprising a main arm connected to the stand and an auxiliary arm operatively connected to the main arm, a table which mounts at least part of the medical equipment having a table area and an underside, and an S-bracket connecting the auxiliary arm to the table such that the auxiliary arm is remote from the table. The auxiliary arm is above the table and the S-bracket comprises a mounting flange, an underside flange and a linking flange connecting the mounting flange to the underside flange. Fasteners connect the underside flange to the table.

From the foregoing disclosure and the following more detailed description of various preferred embodiments it will be apparent to those skilled in the art that the present invention provides a significant advance in the technology and art of stands for medical equipment. Particularly significant in this regard is the potential the invention affords for providing a high quality, low cost, easy to use stand adapted for specialized design constraints, including wheelchair bound patients. Additional features and advantages of various preferred embodiments will be better understood in view of the detailed description provided below.

Figure 1:
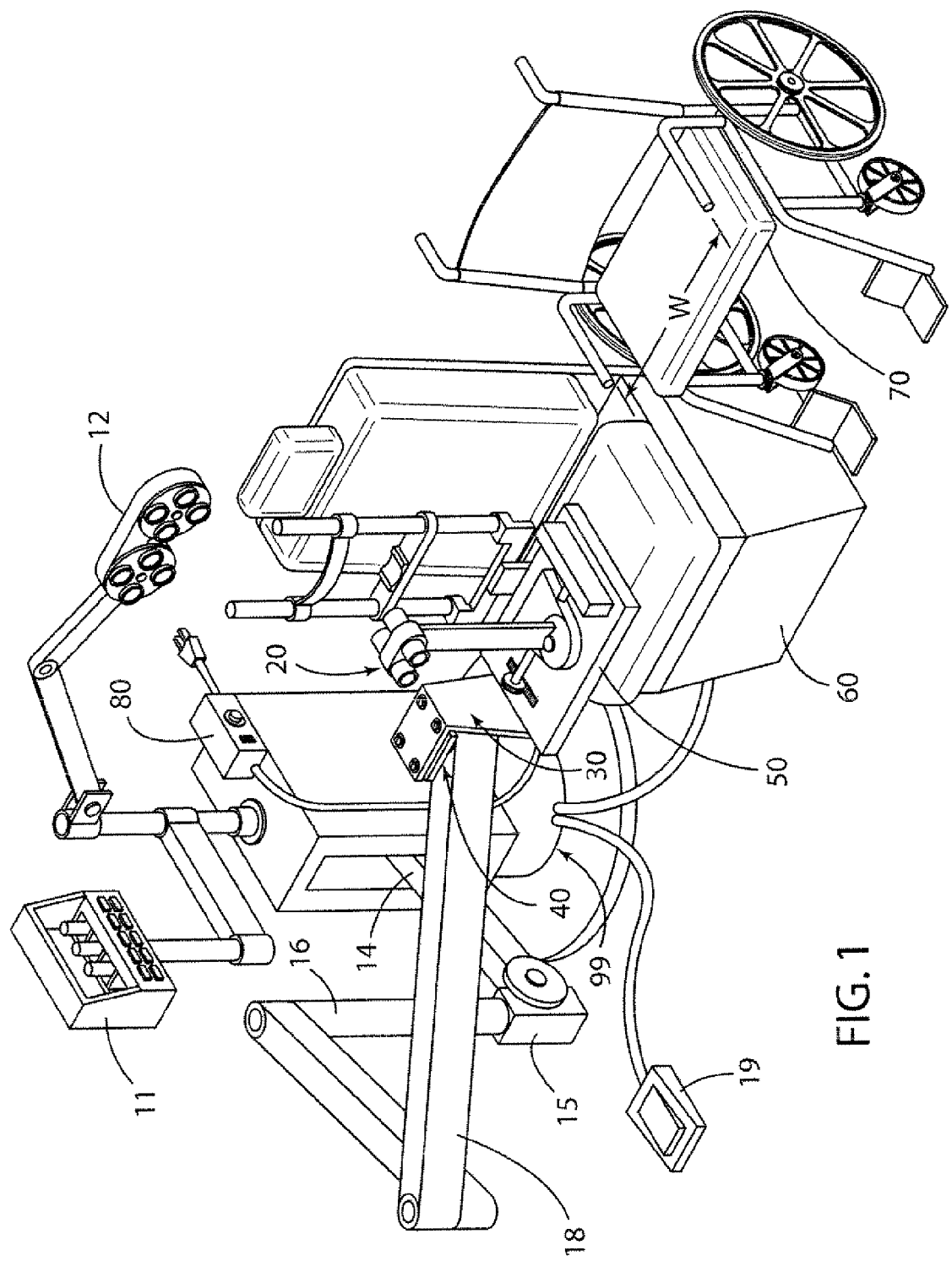
FIG. 1 is a schematic perspective view of a preferred embodiment of a patient examination assembly with a stand and an examination chair, where the medical device is a slit lamp biomicroscope positioned on a table.

It should be understood that the appended drawings are not necessarily to scale, presenting a somewhat simplified representation of various preferred features illustrative of the basic principles of the invention. The specific design features of the patient examination assembly as disclosed here will be determined in part by the particular intended application and use environment. Certain features of the illustrated embodiments have been enlarged or distorted relative to others to help visualization and clear understanding. In particular, thin features may be thickened, for example, for clarity of illustration. All references to direction and position, unless otherwise indicated, refer to the orientation illustrated in the drawings.

DETAILED DESCRIPTION OF CERTAIN PREFERRED EMBODIMENTS

It will be apparent to those skilled in the art, that is, to those who have knowledge or experience in this area of technology, that many uses and design variations are possible for the medical equipment stand disclosed here. The following detailed discussion of various alternative and preferred features and embodiments will illustrate the general principles of the invention with reference to a stand for use with an ophthalmic slit lamp. Other embodiments suitable for other applications, such as a stand for use with an ocular blood flow analyzer will be apparent to those skilled in the art given the benefit of this disclosure.

Referring now to the drawings, FIG. 1 shows a patient examination assembly in accordance with a preferred embodiment. A stand 10, preferably rotatable about a vertical axis, receives an arm assembly and other medical equipment. In FIG. 1, some of the medical equipment can comprise, for example, a control panel and storage chamber 11, as well as a phoropter 12, (the instrument used by optometrists and opthalmologists to measure an individual's refractive error and determine his eyeglass prescription) are mounted on the stand 10. The arm assembly operatively connects the stand to an S-bracket 30 and comprises, for example, a main arm 14 which is adjustable up and down, a linking arm 15, an elbow arm 16 which is preferably rotatable with respect to the linking arm 15, and an auxiliary arm 18. Additional combinations of arms can be used to operatively connect the table 50 and stand 10. The S-bracket is attached to the auxiliary arm at a free end of the auxiliary arm 18, remote from the pivot connection between the auxiliary arm 18 and the elbow arm 16. The table 50 is in turn connected to the S-bracket. Additional medical equipment, here, for example, a slit lamp biomicroscope 20, is mounted on the table 50.

FIG. 1 shows a standard wheelchair 70 having a gap w between its arms. This standard length is about 15.5 inches. Heretofore known slit lamp biomicroscopes could not fit between the arms of the standard wheelchair in part because the table was too wide. In accordance with a highly advantageous feature, the width 52 of the table 50 is reduced to less than the gap w between the arms of a standard wheelchair. Most preferably, the table width is about 1.5-3.5 inches less than the gap w between the arms, or 12-14 inches wide.

Figure 2:
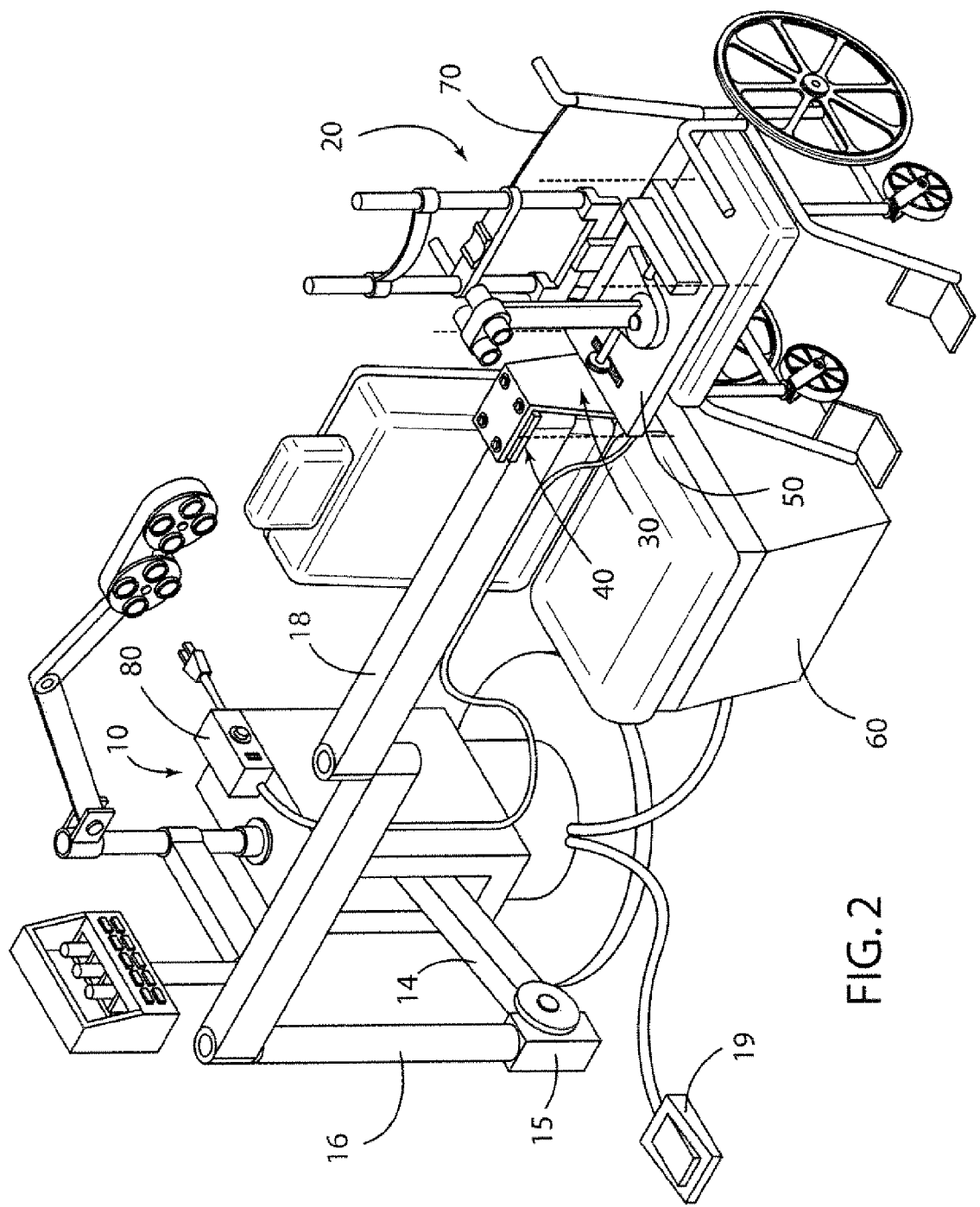
FIG. 2 shows a view of a wheelchair positioned generally adjacent the examination chair and a series of arms connecting the stand and the table such that medical equipment on the table is positioned conveniently for a wheelchair bound patient.
Figure 4:
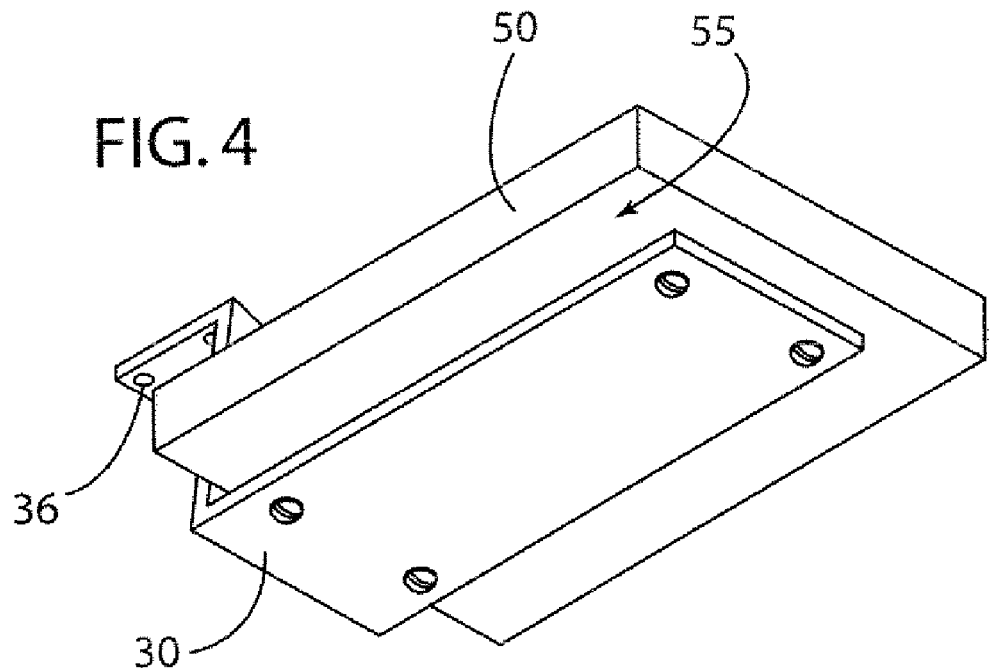
FIG. 4 is an underside view of the table showing the S-shaped bracket mounted to the table.

In accordance with another highly advantageous feature, the auxiliary arm 18 is positioned remote from the table 50. More specifically, the table defines a table area and, as seen in FIG. 2, the auxiliary arm 18 is not positioned within a column defined by the volume above and especially below the table area (shown by the dashed vertical lines of FIG. 2). Advantageously, all equipment except for the thin S-bracket is removed from the underside 55 of the table 50. Also, as shown best in FIGS. 1 and 2, preferably the auxiliary arm is above the table (but also remote from the table). Also, a transformer 80 which controls power to the slit lamp may advantageously be removed from the known mounting location on an underside of the table and moved free of the underside of the table, such as to the stand 10. Thus, the only component of the patient examination assembly underneath the table 50 now is an underside flange 34 of the S-bracket 30, and this flange has a thin cross section. FIG. 4 shows the view of the underside flange 34 attached to the underside 55 of the table 50 with fasteners 78. This combination of improvements has the overall effect of allowing wheelchair bound patients to be examined without the need for removing them from their wheelchair. The distance between the table 50 and the ground or floor can be reduced from about 32 inches (without significant manual deflection of the arm assembly) to about 25 inches. This, plus the improvements in the mounting locations which clear out the space under the table allow for the existing medical equipment (slit lamp biomicroscope, etc.) to be readily used with wheelchair bound patients.

Figure 3:
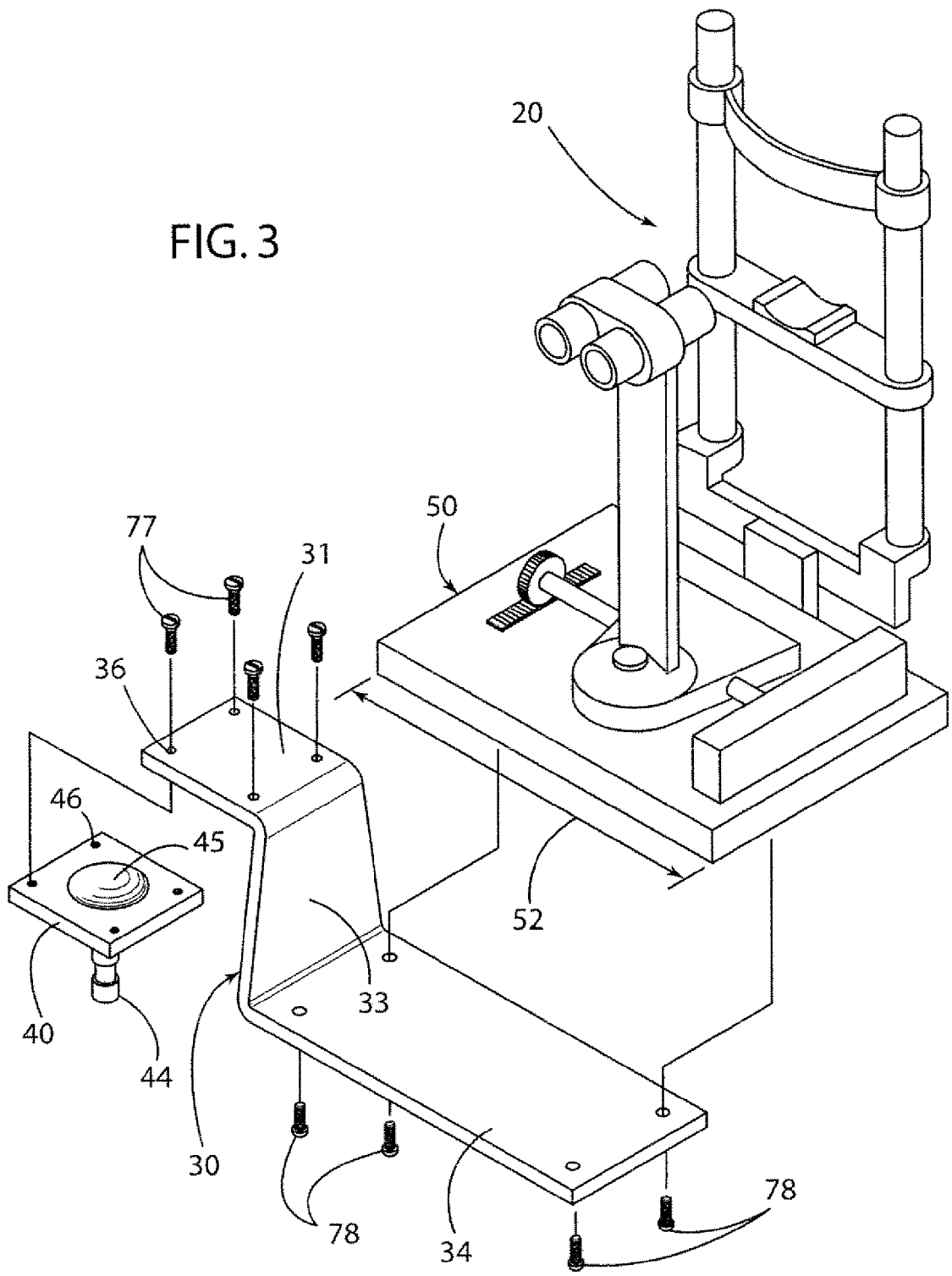
FIG. 3 is a partial exploded perspective view of an S-shaped bracket, a mounting bracket and fasteners which connect the S-shaped bracket to the table and fasteners which connect the S-shaped bracket and mounting bracket to the auxiliary arm.

FIG. 3 shows the S-bracket 30 and its connection to the table 50 in more detail. The S-bracket 30 has a mounting flange 31, a linking flange 33 and an underside flange 34. Preferably the mounting flange 31 is generally horizontal with the ground (or the floor), the linking flange 33 is generally vertical with the ground, and the underside flange 34 is generally horizontal with the ground and parallel to the underside 55 of the table 50. This allows the S-bracket to be conveniently mounted to the auxiliary arm 18 and to the underside 55 of the table 50. A mounting bracket 40 is preferably positioned between the auxiliary arm 18 and the mounting flange 31 of the S-bracket 30. A pin 44 extends from the mounting bracket 40 and engages and opening in the auxiliary arm 18. Optionally a set screw (not shown) may be provided at the auxiliary arm which engages the pin 44 to help secure the mounting bracket/S-bracket/table to the auxiliary arm.

Figure 5:
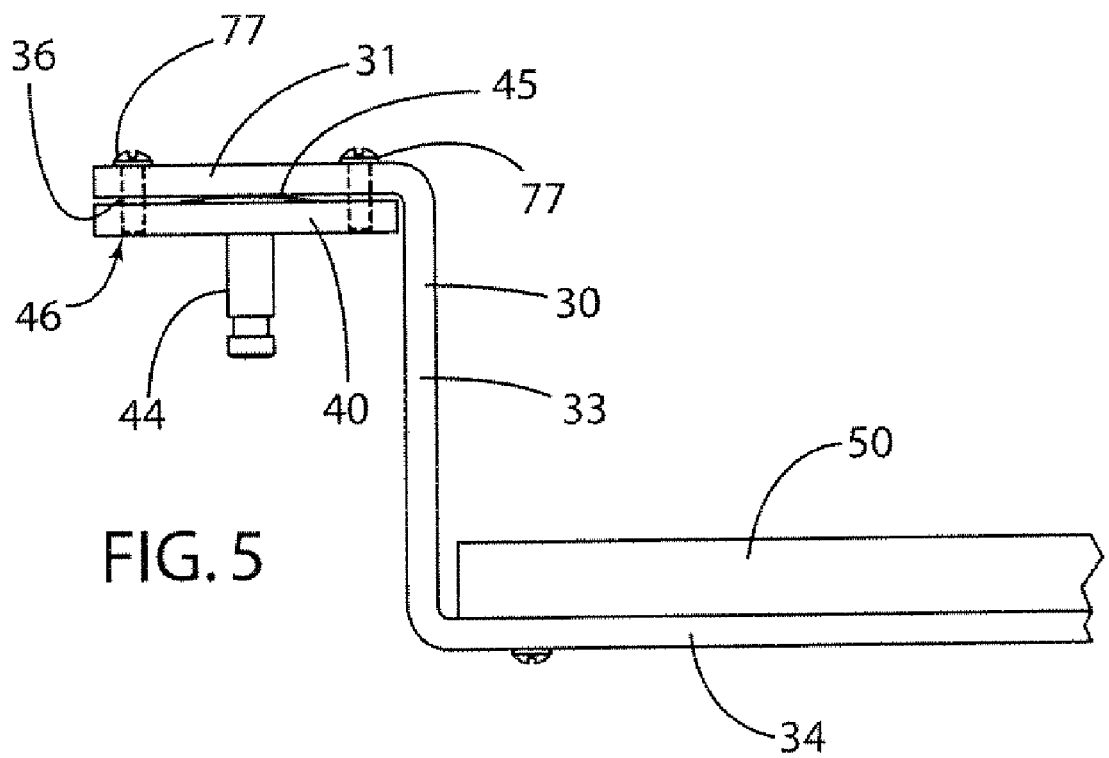
FIG. 5 is a close up partial side view of the connection between the S-shaped bracket and the table.

FIG. 5 shows one preferred embodiment where a hump 45 extends vertically from the mounting bracket 40. The mounting flange 31 sits on the hump 45 to produce a gap between the mounting bracket and the mounting flange 31 of the S-bracket 30 as shown. Advantageously, this allows for deflection of the S-bracket with respect to the mounting bracket. This allows for some additional adjustment of the table with respect to a patient. Fasteners 77 may extend through openings 46 in the mounting bracket 40 and openings 36 in the S-bracket 30. The openings may be either threaded or smooth, as desired. For example, openings 46 on the mounting bracket 40 may be threaded and openings 36 on the S-bracket not threaded. Also, the fasteners may preferably be screws having round heads to avoid creating rough surfaces. Optionally, lock nuts (not shown) may be provided on fasteners 77.

From the foregoing disclosure and detailed description of certain preferred embodiments, it will be apparent that various modifications, additions and other alternative embodiments are possible without departing from the true scope and spirit of the invention. The embodiments discussed were chosen and described to provide the best illustration of the principles of the invention and its practical application to thereby enable one of ordinary skill in the art to use the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A patient examination assembly comprising, in combination:
   a rotatable stand which receives a slit lamp microscope;
   an arm assembly mounted on the stand comprising a main arm connected to the stand and an auxiliary arm operatively connected to the main arm;
   a table which mounts at least part of the a slit lamp microscope having a table area and an underside;
   a mounting bracket attached to the auxiliary arm; and
   a bracket connecting the auxiliary arm to the table such that the auxiliary arm is remote from the table, wherein the bracket comprises a mounting flange attached to the mounting bracket and an underside flange attached to the underside of the table and operatively connected to the mounting flange.

2. The patient examination assembly of claim 1 wherein the auxiliary arm is above the table.

3. The patient examination assembly of claim 1 further comprising
   a pin extending from the mounting bracket and engaging the auxiliary arm; and
   a hump extending from the mounting bracket, wherein the hump engages the mounting flange to produce a gap between the mounting bracket and the mounting flange of the bracket when assembled, which allows for deflection of the bracket with respect to the mounting bracket.

4. The patient examination assembly of claim 1 wherein the table has a width of less than 15.5 inches.

5. The patient examination assembly of claim 4 wherein the table has a width of about 12-14 inches.

6. The patient examination assembly of claim 1 further comprising a transformer positioned free of the underside of the table.

7. The patient examination assembly of claim 1 wherein the bracket further comprises a linking flange connecting the mounting flange to the underside flange, wherein fasteners connect the underside flange to the table.

8. A patient examination assembly comprising, in combination:
- a rotatable stand which receives medical equipment;
- an arm assembly mounted on the stand comprising a main arm connected to the stand and an auxiliary arm operatively connected to the main arm;
- a table which mounts at least part of the medical equipment having a table area and an underside;
- an S-bracket connecting the auxiliary arm to the table such that the auxiliary arm is remote from the table, wherein the S-bracket comprises a mounting flange, an underside flange and a linking flange connecting the mounting flange to the underside flange, wherein fasteners connect the underside flange to the table; and a mounting bracket positioned between the auxiliary arm and the S-bracket, operatively connecting the S-bracket to the auxiliary arm.

9. The patient examination assembly of claim 8 further comprising a pin extending from the mounting bracket and engaging the auxiliary arm.

10. The patient examination assembly of 8 further comprising a hump extending from the mounting bracket, wherein the hump engages the mounting flange to produce a gap between the mounting bracket and the mounting flange of the S-bracket when assembled, which allows for deflection of the S-bracket with respect to the mounting bracket.

\* \* \* \* \*